United States Patent [19]

Battista

[11] 4,231,381
[45] Nov. 4, 1980

[54] DENTAL FLOSS AND DENTAL AID HOLDER

[76] Inventor: Orlando A. Battista, 5280 Trail Lake Dr., Fort Worth, Tex. 76133

[21] Appl. No.: 965,820

[22] Filed: Dec. 4, 1978

[51] Int. Cl.³ .............................................. A61C 15/00
[52] U.S. Cl. ...................................................... 132/89
[58] Field of Search ................. 132/89, 79; 32/40 R; 220/23; 206/63.5, 229, 380, 210

[56] References Cited

U.S. PATENT DOCUMENTS

| 1,858,134 | 5/1932 | Booth et al. | 132/79 E |
| 4,040,433 | 8/1977 | Edison | 132/89 |
| 4,165,815 | 8/1979 | Vetter | 220/23 |

*Primary Examiner*—Robert Peshock
*Attorney, Agent, or Firm*—E. Janet Berry; Lawrence Rosen

[57] ABSTRACT

A throw-away dental aid article includes a container body adapted to store a supply of a liquid mouthwash therein. The open neck of the container is threaded. A closure cap has a compartment therein for the storage of a supply of dental floss and is threaded so as to be releasably secured to the container. A toothpick is connected to the closure cap to depend therefrom and extend into the container when the closure cap is secured thereto. Access to the compartment in the closure cap is provided by an aperture in the top wall of the closure cap which is normally closed by a removable cap.

10 Claims, 5 Drawing Figures

DENTAL FLOSS AND DENTAL AID HOLDER

BACKGROUND OF THE INVENTION

The invention relates to dental aid articles and more particularly to a disposable composite article capable of storing supplies of dental floss and a liquid mouthwash and also incorporating a toothpick.

Composite dental aid articles have been known heretofore which provide for the storage of dental floss in a cap section and dentifrice in a tube or body section which is separable from the cap. However, such prior articles were not capable of use as a throw-away article since they were relatively expensive to manufacture and designed to store sufficient dental floss and dentifrice to accommodate multiple usage. A typical prior article is shown in U.S. Pat. No. 1,858,134, issued May 10, 1932 to H. N. Booth et al. The cap of the article is apertured to permit the removal of a length of dental floss. In order to protect the dental floss against the intrusion of dirt and dust through the aperture in the cap a disk was provided which was positioned within the cap above the dental floss. The resulting structure was thus complex and relatively expensive. Further, there was no provision for a toothpick which has been found to be a valuable adjunct to the dental floss. Other prior composite articles which have been known heretofore are similarly or comparably disadvantageous.

SUMMARY OF THE INVENTION

It is the principal object of this invention to provide a dental aid article of the composite type which is relatively inexpensive to manufacture and capable of use as a throw-away after a single usage.

It is another object of the invention to provide a dental aid article capable of use as a throw-away after single usage which is of simple construction and in addition to storing supplies of dental floss and mouthwash provides an integrally formed and easily manipulable toothpick.

It is still another object of the invention to provide a throw-away composite dental aid article which preserves the sterility of all of its contents until placed in use.

Yet another object of the invention is the provision of a plurality of dental aid articles of the character described which are interconnected to thereby make available sufficient dental aid material for a plurality of usages while concomitantly preserving the hygienic integrity of each composite article.

Other objects and advantages of the invention will become readily apparent to persons versed in the art from the ensuring description.

According to the present invention there is provided a throw-away composite dental aid article comprising in combination:

a container body adapted to store therein a supply of mouthwash, said container having a threaded open end;

a closure cap including a compartment for dental floss defined by a peripherally extending side wall, a bottom wall and an apertured top wall, said closure cap having a depending skirt which is threaded to engage cooperably with the threaded portion of the container body to releasably secure the closure cap thereto;

a toothpick connected to said closure cap so as to depend therefrom and extend into said container when the closure cap is secured thereto;

and a cap dimensioned and configured to seat within the aperture of the top wall of said closure cap to selectively provide access to the interior of said compartment.

BRIEF DESCRIPTION OF THE DRAWINGS

In order that the invention may be more fully comprehended it will now be described, by way of example, with reference to the accompanying drawings in which.

DESCRIPTION OF THE PREFERRED EMBODIMENTS

Figure 1:
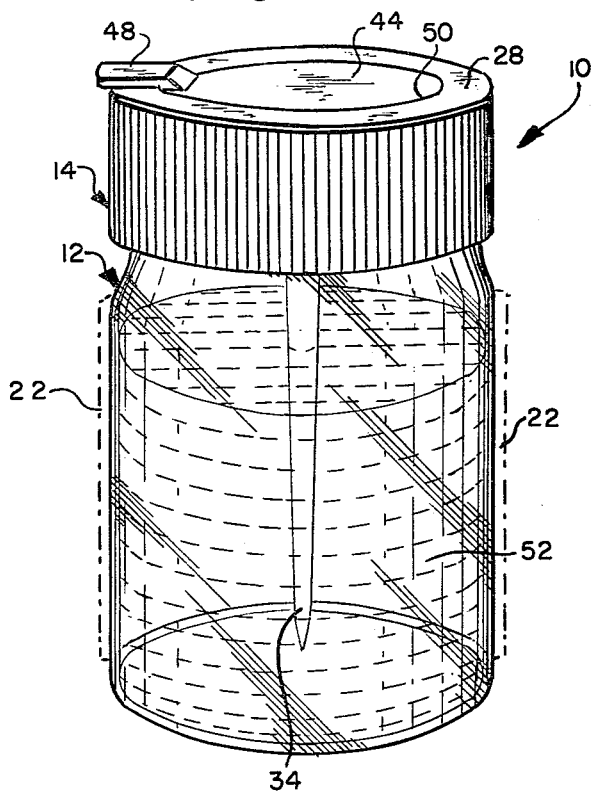
FIG. 1 is a front elevational view of a composite dental aid article embodying the features of the invention.
Figure 2:
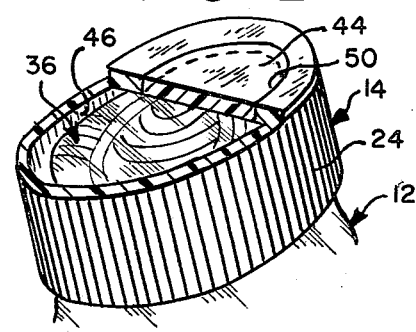
FIG. 2 is a perspective view of the upper portion of the dental aid article shown in FIG. 1 with the top of the closure cap broken away to show its compartment and the contents thereof.

Referring to the drawings there is shown a composite dental aid article identified generally by reference numeral 10. Such article includes a container body 12 and a closure cap 14.

The container body 12 and desirably also the closure cap 14 are formed of a conventional synthetic plastics material. It will be understood that the particular plastics material selected is not critical; however, the material should possess sufficient rigidity or the walls of at least the upper portion of the container body and the corresponding portion of the closure cap should have adequate thickness such that they are capable of threadedly cooperating to releasably secure the closure cap to the container body as will become clear.

Figure 5:
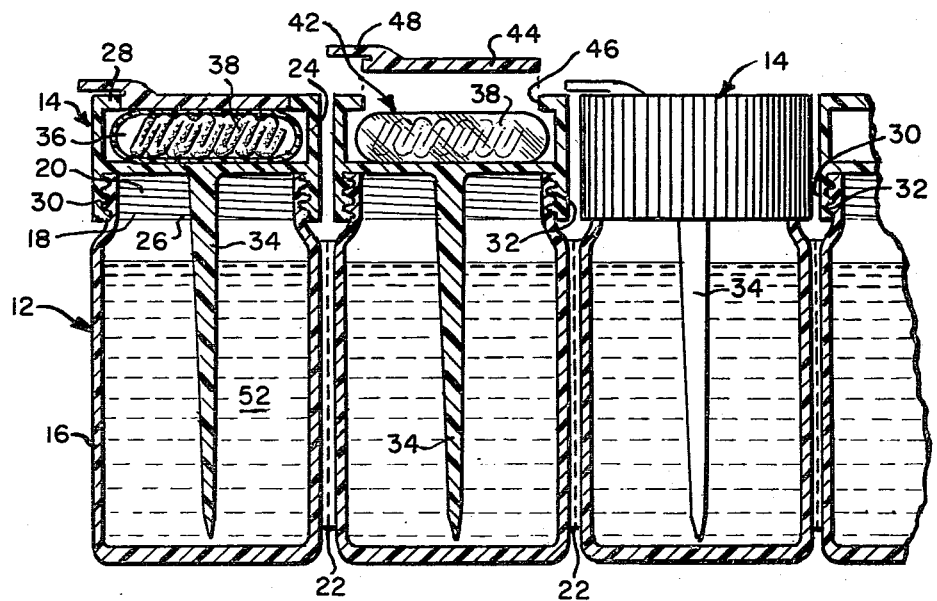
FIG. 5 is a front elevational view showing a series of interconnected dental aid articles of the invention and the dental aid materials therein.

The container body 12 may be formed of generally cylindrical configuration although when fabricated with a thin sidewall structure it will be apparent that the lower section 16 may adopt other shapes. The upper section 18 will in all instances be cylindrical and provided with threads 20 for receiving thereon the closure cap 14. In a presently preferred embodiment as illustrated in FIG. 5 the container bodies are simultaneously molded or molded in such fashion as to produce a series of such bodies which are interconnected at their sidewalls by marginal strips 22 which can easily be ruptured so as to readily separate one container body from the adjacent connected container body. Alternatively, the containers may be produced individually with such marginal strips and subsequently joined therealong by thermasealing according to known techniques. However, it is important to provide for the ready separation of the container bodies along strips 22 when so desired. This can, of course, be effectuated either by incorporating weakened zones in such strips or by providing the strips in a thickness which is less than the thickness of the sidewalls of the container bodies. Any other expedient for insuring quick and easy separation of the container bodies may be utilized. It will be understood, however, that the container bodies need not necessarily be fabricated with strips 22 to enable series interconnection.

The closure cap 14 is formed with a peripherally extending sidewall 24, bottom wall 26 and top wall 28. A skirt 30 depends from the closure cap and has formed thereon threads 32 which are cooperable with the threads on the container body so that the closure cap may be releasably secured thereto. Affixed to the bottom wall 26 of the closure cap is a toothpick member 34. The toothpick projects substantially perpendicularly from the closure cap so as to extend into the container body when the closure cap is applied. Desirably the closure cap is formed of a synthetic plastics material and is molded integrally with the toothpick.

Figure 3:
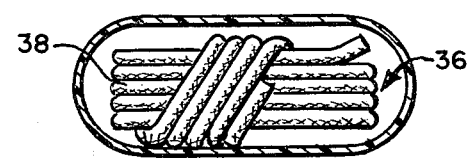
FIG. 3 is a top plan view of the compartment in the closure cap with its cap removed to show the disposition of its contents.
Figure 4:
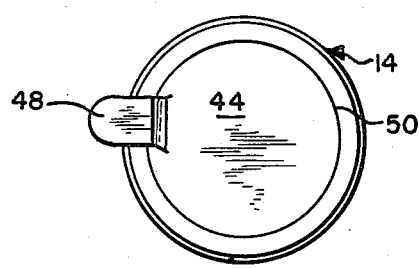
FIG. 4 is a top plan view of the closure cap with its removable cap in sealed position.

The closure cap 14 is provided with a cavity or compartment 36 for the disposition therewithin of a supply of dental floss 38. In the preferred form of the invention a length of dental floss sufficient for a single usage is packaged within a plastic wrapping such as polyethylene and is disposed within compartment 36 such as in the coiled form shown in FIG. 3. It will be appreciated that the compartment may occupy all or less than the volume between the top, bottom and side wall of the closure cap as may be found most desirable. The top wall of closure cap 14 is formed with an aperture 42 therein which may, if so desired, be substantially coterminous with the size and shape of compartment 36. A cap 44 is provided for sealing the aperture 42 and is desirably of such demensions that it seats with respect to the annular edge 46 of the top wall by a force-fit. The cap 44 is thus selectively removable to allow access to the dental floss within compartment 36. For convenience a tab element 48 may be formed on cap 44 which tab projects outwardly to overlie the top and side walls of the closure cap for easy grasping when cap 44 is to be removed. It is within the contemplation of the invention to mold the closure cap 14 and cap 44 in a single step. In such instance the cap 44 may be separable from the closure cap 14 along a zone of weakness 50. If desired the cap 44 may be molded in such manner that there is a living hinge between same and the closure cap such that access to compartment 36 may be permitted without complete separation of the cap 44 from closure cap 14.

Prior to screwing closure cap 14 onto the container body 12 the hollow container body is filled with a quantity of a liquid mouthwash 52. Since the primary use of the composite dental aid article is as a single usage throw-away item, the container body should be dimensioned to provide sufficient volume therewithin to accommodate approximately one fluid ounce of liquid mouthwash material. However, the capacity of the container body may be suitably increased or decreased as may be deemed advisable.

An advantage of the dental aid article of this invention is that because of its simple construction and relatively low cost it may be disposed of after a single use. However, sufficient dental floss and mouthwash may be provided for several applications before disposal of the article. Thus, the article should enjoy widespread use with travellers, lecturers, businessmen, etc. who cannot conveniently carry a toothbrush and mouthwash aid to locations remote from their rooms for the control of immediate after-meal halitosis. The article of the invention can easily be carried in a pocketbook, briefcase, or even in one's pocket so that immediately following a meal any available bathroom facility can be utilized for use of the dental floss and mouthwash components. The article of the invention thus not only enables one to promptly alleviate after-meal oral discomforts, it provides a valuable dental aid in the reduction of dental caries.

Although the invention has been described in specific terms it will be understood that various changes may be made in size, shape, materials and in the arrangement of the parts without departing from the spirit and scope of the invention as claimed.

What is claimed is:

1. A throw-away composite dental aid article comprising in combination:

a container body for storing therewithin a supply of mouthwash, said container having a threaded open end;

a closure cap including a compartment containing dental floss said compartment defined by a peripherally extending side wall, a bottom wall and a top wall having an aperture therein, said closure cap having a depending skirt which is threaded to engage cooperably with the threaded portion of the container body to releasably secure the closure cap thereto;

a toothpick connected to the said bottom wall of said closure cap so as to depend therefrom and extend into said container when the closure cap is secured thereto;

and a cap dimensioned and configured to seat within said aperture aperture of the top wall of said closure cap to selectively provide access to the interior of said compartment.

2. A dental aid article according to claim 1, wherein said closure cap and container body are formed from a synthetic plastics material.

3. A dental aid article according to claim 1 or 2, wherein the container body is secured along at least one of the sidewalls thereof to the sidewall of an adjacently disposed container body of a like dental aid article.

4. A dental aid article according to claim 1 or 2, wherein the cap for the aperture in the top wall of said closure cap is dimensioned to seat within the aperture with a force-fit.

5. A dental aid article according to claim 3 wherein the cap for the aperture in the top wall of said closure cap is dimensioned to seat within the aperture with a force-fit.

6. A dental aid article according to claim 4, including a tab for said cap which projects outwardly so as to overlie the top and side wall of the closure cap.

7. A dental aid article according to claim 5, including a tab for said cap which projects outwardly so as to overlie the top and side wall of the closure cap.

8. A dental aid article according to claim 1 including a supply of dental floss stored within said compartment and a supply of a liquid mouthwash stored within said container body.

9. A dental aid article according to claim 3, including a plurality of said container bodies which have been simultaneously molded and form a series of connected readily separable units.

10. A dental aid article according to claim 1, wherein said toothpick is connected to the bottom wall of said closure cap so as to depend therefrom.

* * * * *